United States Patent [19]

Bey et al.

[11] 4,342,780
[45] Aug. 3, 1982

[54] METHOD OF DEPLETING ENDOGENOUS MONOAMINES

[75] Inventors: Philippe Bey, Strasbourg; Michel Jung, Illkirch-Graffenstaden, both of France

[73] Assignee: Merrell-Toraude et Cie, Strasbourg, France

[21] Appl. No.: 235,275

[22] Filed: Feb. 17, 1981

Related U.S. Application Data

[63] Continuation-in-part of Ser. No. 91,463, Nov. 5, 1979, abandoned, which is a continuation-in-part of Ser. No. 58,475, Jul. 18, 1979, abandoned, which is a continuation-in-part of Ser. No. 33,719, Apr. 26, 1979, abandoned, which is a continuation-in-part of Ser. No. 814,243, Jul. 8, 1977, abandoned.

[51] Int. Cl.$^3$ .................................................. A61K 31/195
[52] U.S. Cl. ................................................... 424/319
[58] Field of Search ........................................ 424/319

[56] References Cited

U.S. PATENT DOCUMENTS

| | | | |
|---|---|---|---|
| 3,046,300 | 7/1962 | Sletzinger et al. | 562/446 |
| 3,553,258 | 1/1971 | Kaiser et al. | 560/38 |
| 3,746,753 | 7/1973 | Krady et al. | 562/446 |

*Primary Examiner*—Stanley J. Friedman
*Attorney, Agent, or Firm*—David E. Frankhouser; Raymond A. McDonald; William J. Stein

[57] ABSTRACT

2-Amino-2-fluoromethyl-3-(substituted)phenyl propionic acids and derivatives thereof are coadministered with dopamine for the treatment of schizophrenia, mania, tardive dyskinesia, anxiety, or depression.

19 Claims, No Drawings

METHOD OF DEPLETING ENDOGENOUS MONOAMINES

This application is a continuation-in-part of copending application Ser. No. 91,463, filed Nov. 5, 1979, now abandoned, which is a continuation-in-part of application Ser. No. 58,475, filed July 18, 1979, now abandoned, which is a continuation-in-part of application Ser. No. 33,719, filed Apr. 26, 1979, now abandoned, which is a continuation-in-part of application Ser. No. 814,243, filed July 8, 1977, now abandoned.

This invention relates to the use of certain 2-amino-2-fluoromethyl-3-(substituted)phenyl propionic acids and derivatives thereof, which are irreversible inhibitors in vivo of aromatic amino acid decarboxylase (AADC) for depleting endogenous monoamines in the central nervous system (CNS) in the treatment of certain neuropsychiatric disorders. It is well known that certain monoamines of the catecholamine type—dopamine, norepinephrine, and epinephrine—are synthesized in vivo from tyrosine by a metabolic process in which an intermediate step is the decarboxylation of 3,4-dihydroxyphenylalanine (dopa), a reaction catalyzed by AADC. Since dopamine is converted to norepinephrine, which in turn is converted to epinephrine, blockade of the decarboxylation step, such as by inhibition of AADC, can provide a method for regulating the endogenous levels of the catecholamines in body tissue. In addition to catalyzing the decarboxylation of dopa, AADC is also known to catalyze the decarboxylation of other aromatic amino acids to give other types of monoamines—namely, tyrosine, phenylalanine, tryptophan, and 5-hydroxytryptophan (5-HTP). Hence, inhibition of AADC also provides a method for regulating in vivo the endogenous levels of tyramine and phenethylamine, as well as the indoleamines-tryptamine and 5-hydroxytryptamine (5-HT). The endogenous monoamines formed by the action of AADC are involved in various physiological processes, and certain clinically important neuropsychiatric disorders are known to be related to an imbalance of a particular monoamine in the CNS. Administration of an AADC inhibitor having central activity will therefore provide a method for controlling such disorders by regulating the level of the endogenous monoamine.

Although it is desirable to deplete central monoamine levels in the treatment of neuropsychiatric disorders, the use of an AADC inhibitor to effect such depletion will also cause depletion of peripheral monoamine levels, which depletion can produce various undesirable side effects. The present invention provides an effective method for depleting endogenous monoamine levels centrally while eliminating or reducing the undesirable side effects associated with the peripheral effects produced by the inhibitor.

The invention sought to be patented comprehends a method for controlling certain neuropsychiatric disorders in mammals in need thereof, said disorders being schizophrenia, mania, tardive dyskinesia, anxiety, or depression which comprises administering to said mammals:

(a) an effective amount of an α-fluoromethyl amino acid derivative having the formula:

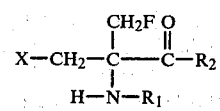

wherein:

$R_1$ is hydrogen, ($C_1$–$C_4$alkyl)carbonyl, or

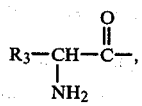

wherein $R_3$ is hydrogen, $C_1$–$C_8$alkyl, benzyl, or 4-hydroxybenzyl; $R_2$ is hydroxy, $C_1$–$C_8$ alkoxy, amino, ($C_1$–$C_4$alkyl)amino, di($C_1$–$C_4$alkyl)amino, or

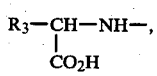

wherein $R_3$ is hydrogen, $C_1$–$C_8$alkyl, benzyl, or 4-hydroxybenzyl; X is a substituted phenyl group of the formula:

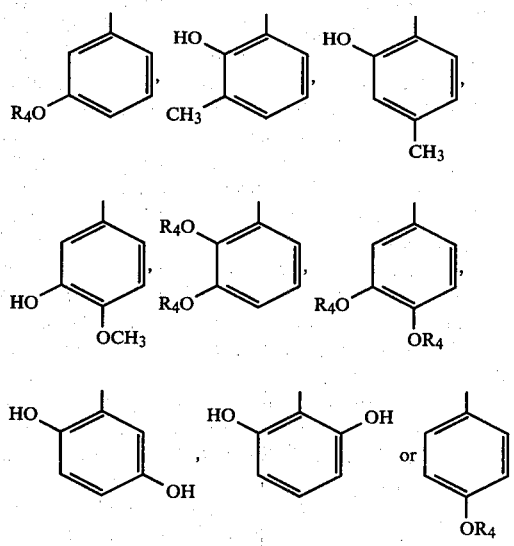

wherein $R_4$, as defined by X, is hydrogen, ($C_1$–$C_4$alkyl)carbonyl, benzoyl, or phenyl($C_1$–$C_6$alkylene)carbonyl; and the pharmaceutically acceptable salts thereof; and the individual optical isomers thereof; with (b) an effective amount of dopamine.

The compounds of Formula I are irreversible inhibitors of AADC enzyme in vivo and are capable of depleting levels of endogenous monoamines in the CNS. The compounds are useful for treating those neuropsychiatric disorders which are associated with elevated levels of endogenous monoamines in the CNS. However, at doses which normally deplete endogenous monoamines centrally, the compounds of Formula I may also deplete endogenous catecholamines peripherally. Thus in the treatment of neuropsychiatric disorders by the administration of a compound of Formula I, peripheral catecholamines can also be depleted resulting in the occurrence of certain undesirable side effects such as hypotension, malaise, or sexual disfunction. The administration of exogenous dopamine and a compound of Formula I in accordance with the present invention restores peripheral catecholamine levels which otherwise would have been depleted because of the peripheral inhibition of AADC. Thus, the invention provides a method of treating neuropsychiatric disorders whereby central endogenous monoamines are depleted without the production of the undesirable side effects which are usually associated with the depletion of catecholamines peripherally.

As used herein the term "central" refers to the central nervous system, primarily the brain, in which aromatic amino acid decarboxylase enzymes are present. Additionally, as used with regard to the utility of this invention, the term "central" also refers to the various effects that an imbalance of monoamines has upon the central nervous system and the various physiological disorders resulting therefrom. The term "peripheral" refers to various other target organs or target tissues, as for example the heart or kidneys, in which aromatic amino acid decarboxylase enzymes are present. The term "monoamines" as used herein refers to the catecholamines —dopamine, epinephrine, and norepinephrine, to the indoleamines—tryptamine and 5-hydroxytryptamine, and to tyramine and phenethylamine, which substances are metabolically derived from the corresponding endogenous amino acids via the action of AADC.

The term "neuropsychiatric disorders" refers broadly to abnormal or diseased conditions relating to the mind-body relationship that are considered to be primarily associated with an elevation of monoamine levels in the CNS, and in particular, the brain. The term "neuropsychiatric disorders" contemplates the following diseases or dysfunctions: schizophrenia, mania, tardive dyskinesia, anxiety, and depression. It is recognized that these conditions are not attributable solely to the central nervous system, but may also have peripheral components, as for example, in anxiety. However, the practice of this invention is understood to be directed to those uses, which are primarily central in origin, but not necessarily exclusive thereof.

Examples of the neuropsychiatric disorders which can be treated according to the method of this invention and the monoamines believed to be associated with such disorders are:

(a) Schizophrenia which is associated with elevated central levels of dopamine, penethylamine and/or dimethyltryptamine (formed by enzymatic methylation of tryptamine).

(b) Mania which is associated with elevated central levels of norepinephrine and/or 5-hydroxytryptamine[- See Rosenblatt et al., *J. Psychiat. Res.*, 6, 321 (1969) and Brodie *Clin. Pharmacol. and Therapeutics*, 12, 218 (1971)].

(c) Seizure disorders (such as tardive dyskinesia) which are associated with elevated central levels of tyramine and/or dopamine.

(d) Anxiety which is associated with elevated central levels of epinephrine, norepinephrine, and/or phenethylamine [See Breggin, *J. Neur. Ment. Dis.*, 139, 558 (1964)].

Preferred compounds of Formula I for the methods described and claimed herein are those wherein $R_1$ is hydrogen or ($C_1$-$C_4$alkyl)carbonyl, $R_2$ is hydroxy or $C_1$-$C_8$ alkoxy, and $R_4$ is hydrogen. Hence, in its preferred subgeneric aspects, the invention contemplates the classes of compounds of formula I wherein, $R_1$, $R_2$, and $R_4$ are defined as follows:

(1) $R_1$ is hydrogen, and $R_2$ is hydroxy.
(2) $R_1$ is hydrogen, $R_2$ is hydroxy, and $R_4$ is hydrogen.
(3) $R_2$ is hydroxy and $R_4$ is hydrogen.
(4) $R_1$ is ($C_1$-$C_4$alkyl)carbonyl, $R_2$ is hydroxy, and $R_4$ is hydrogen.
(5) $R_1$ and $R_4$ are hydrogen.
(6) $R_1$ is hydrogen, $R_2$ is $C_1$-$C_8$alkoxy, and $R_4$ is hydrogen.

Preferred substituted phenyl groups defined by X are:

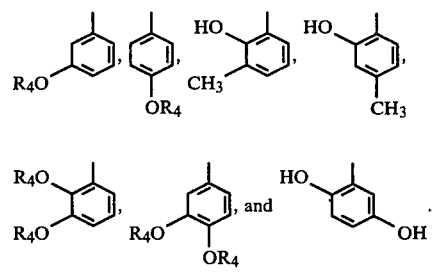

It should be recognized that the compounds of Formula I, wherein $R_1$ is hydrogen, $R_2$ is hydroxy, and $R_4$ is hydrogen, are the compounds which inhibit AADC in vitro and which therefore actually interact with the AADC enzyme in vivo. The compounds of Formula I wherein either $R_1$ or $R_4$ is a group other than hydrogen or wherein $R_2$ is a group other than hydroxy do not inhibit AADC in vitro and must be transformed in vivo by chemical or enzymatic action to a compound which contains a terminal carboxyl group ($R_2$ is hydroxy), a free α-amino group ($R_1$ is hydrogen), and at least one free hydroxy group ($R_4$ is hydrogen) in the phenyl ring. It will be apparent to those skilled in the art that any compound of Formula I, which contains a group substituted at the α-amino group forming an amide bond ($R_1$) or a group substituted at the terminal carboxylic acid group forming an ester or amide bond ($R_2$), or a group substituted at the aromatic hydroxy group forming an ester group ($R_4$), may be employed for the purposes of this invention, provided that such group is removable in vivo by chemical or enzymatic action.

Illustrative ($C_1$-$C_4$alkyl)carbonyl groups are acetyl, n-propionyl, i-propionyl and n-butyryl. Acetyl or n-butyryl is preferred. Illustrative $C_1$-$C_8$alkoxy groups are methoxy, ethoxy, n-propoxy, i-propoxy, n-butoxy, n-pentyloxy, n-hexyloxy, n-heptyloxy, and n-octyloxy. Illustrative $C_1$-$C_8$ alkyl groups are methyl, ethyl, n-propyl, i-propyl, n-butyl, n-pentyl, n-hexyl, n-heptyl, and n-octyl. Methyl is preferred. Illustrative ($C_1$-$C_4$alkyl)amino groups are methylamino, ethylamino, n-propylamino, i-propylamino, and n-butyl amino. Methylamino is preferred. Illustrative di($C_1$-$C_4$alkyl)amino groups are dimethylamino, diethylamino, di-n-propylamino, or di-n-butylamino. Dimethylamino is preferred. Illustrative groups represented by the formulae:

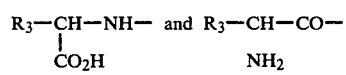

are those moieties derived from the amino acids glycine, alanine, valine, leucine, isoleucine, phenylalanine, or tyrosine.

Illustrative compounds of Formula I which are preferred for use in accordance with this invention are:
2-amino-2-fluoromethyl-3-(2-hydroxy-4-methylphenyl)propionic acid,
2-amino-2-fluoromethyl-3-(2-hydroxy-3-methylphenyl)propionic acid,
2-amino-2-fluoromethyl-3-(3-hydroxy-4-methoxyphenyl)propionic acid,
2-amino-2-fluoromethyl-3-(3-hydroxyphenyl)propionic acid,
2-amino-2-fluoromethyl-3-(3,4-dihydroxyphenyl)propionic acid,
2-amino-2-fluoromethyl-3-(2,3-dihyroxyphenyl)propionic acid,
2-amino-2-fluoromethyl-3-(2,5-dihydroxyphenyl)propionic acid,
2-amino-2-fluoromethyl-3-(2,6-dihydroxyphenyl)propionic acid and,
2-amino-2-fluoromethyl-3-(4-hydroxyphenyl)propionic acid methyl ester or ethyl ester.

Illustrative examples of pharmaceutically acceptable salts of this invention include non-toxic acid addition salts formed with inorganic acids, such as, hydrochloric, hydrobromic, sulfuric and phosphoric acid, and organic acids, such as, methane sulfonic, salicylic, maleic, malonic, tartaric, citric and ascorbic acids; and non-toxic salts formed with inorganic or organic bases such as those of alkali metals, for example, sodium, potassium and lithium, alkaline earth metals, for example, calcium and magnesium, light metals of Group III A, for example, aluminium, organic amines, such as, primary, secondary or tertiary amines, for example, cyclohexylamine, ethylamine, pyridine, methylaminoethanol, ethanolamine and piperazine. The salts are prepared by conventional means.

2-Amino-2-fluoromethyl-3-(4-hydroxyphenyl)propionic acid methyl ester has surprisingly been found to lower engenous catecholamine levels in the brain but not in the heart, while endogenous 5-HT levels in the brain are not altered. Because of this unique selectivity, 2-amino-2-fluoromethyl-3-(4-hydroxyphenyl)propionic acid methyl ester, and the alkyl ester homologs thereof, may be particularly useful for the treatment of the neuropsychiatric disorders associated with elevated brain catecholamine levels. This selectivity is not found for the corresponding acid ($R_2$ is hydrogen). It is believed that monofluoromethyl-p-tyrosine methyl ester forms 2-amino-2-fluoromethyl-3-(3,4-dihydroxyphenyl)propionic acid in vivo.

The compounds of Formula I can be administered in various manners to achieve the desired effect. The compounds can be administered alone or in the form of pharmaceutical preparations to the patient being treated either orally or parenterally, for example, subcutaneously, intravenously or intraperitoneally. The compounds can be administered by intranasal instillation or by application to mucous membranes such as that of the nose, throat and bronchial tubes, for example, in an aerosol spray containing small particles of a novel compound of this invention in a spray solution or dry powder form.

The amount of novel compound administered will vary and can be any effective amount. Depending on the patient, the condition being treated and the mode of administration, the quantity of novel compound administered may vary over a wide range to provide an effective amount in a unit dosage form. In order to achieve a central irreversible inhibition of aromatic amino acid decarboxylase (AADC), the effective amount of a compound of Formula I will vary from about 0.25 mg/kg to 100 mg/kg of body weight of the patient per day and preferably from about 1 mg/kg to 10 mg/kg. For example, the desired central effect can be achieved by consumption of a unit dosage form, such as, for example, a tablet containing from about 50 mg to 500 mg of a novel compound of this invention taken from 1 to 10 times daily.

Dopamine can be administered concomitantly or sequentially, the dosage depending primarily upon the mode of administration. In general, dopamine is administered concomitantly with the aromatic amino acid decarboxylase inhibitor over a broad range of from about 0.01 to 100 mg/kg of body weight of the patient per day. Preferably, a dosage of from 1 to 20 mg/kg of body weight per day of the dopamine is employed.

In the event that dopamine is to be orally administered, it is desirable to administer a derivative of dopamine, due to the poor oral absorption of dopamine per se. Suitable derivatives include the di-lower alkyl or diaryl esters of the dopamine catechol moiety and/or the lower alkyl and aryl carbamate derivatives of the amino moiety of dopamine. Additionally, the amine moiety of dopamine may be condensed with various L-amino acids such as phenylalanine, alanine, glutamate, tyrosine, glycine, serine and threonine to form a peptide. These various derivatives are all readily absorbed via oral administration and are enzymatically converted to dopamine in the body.

Another preferred method of administering dopamine is via intravenous infusion. Dopamine per se can be administered in considerably smaller amounts ranging from 0.01 to 1.0 mg/kg of body weight of the patient per day. Preferably, an amount of from 0.05 to 0.5 mg/kg of dopamine is administered via intravenous infusion to a patient per day.

As used herein the term patient is taken to mean warm blooded animals such as mammals, for example, cats, dogs, rats, mice, guinea pigs, sheep, horses, bovine cows, and humans.

The solid unit dosage forms can be of the conventional type. Thus, the solid form can be a capsule which can be of the ordinary gelatin type containing a novel compound of this invention and a carrier, for example, lubricant and inert fillers such as lactose, sucrose and corn starch. In another embodiment, the novel compounds are tableted with conventional tablet bases such as lactose, sucrose or corn starch in combination with binders such as acacia, corn starch, potato starch, or alginic acid, and a lubricant such as stearic acid, or magnesium stearate.

For parenteral administration the compounds, may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable or synthetic origin, for example, peanut oil, soybean oil, and mineral oil. In general water, saline, aqueous dextrose, and related sugar solutions, ethanols and glycols such as propylene glycol or polyethylene glycol are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber manufactured by the Dow-Corning Corporation.

For use as aerosols the novel compounds in solution or suspension may be packaged in a pressurized aerosol container together with a gaseous or liquified propellant, for example, dichlorodifluoromethane, dichlorodifluoromethane with dichlorodifluoroethane, carbon dioxide, nitrogen or propane, with the usual adjuvants such as cosolvents, and wetting agents, as may be necessary or desirable. The compounds may also be administered in a non-pressurized form such as in a nebulizer or atomizer.

As indicated hereinabove the compounds of Formula I find particular utility when administered together with exogenous dopamine in which case individual formulations of a compound of Formula I and dopamine may be administered, or both active ingredients may be formulated into a single combination pharmaceutical formulation. In either mode of administration the amount of compound of Formula I as compared to the amount of dopamine administered will vary from about 1:1 to 10:1. A combination formulation may contain an internal portion containing dopamine or a derivative thereof and an outer portion containing a compound of Formula I, each active ingredient being suitably formulated. A particularly suitable combination formulation may be prepared by compressing dopamine or a suitable derivative thereof, optionally with suitable carriers, to a core, providing said core with a laminated coating that is resistant to gastric juice, and applying over the coated core an external layer that contains a compound of general Formula I suitably formulated. Using such a combination formulation the decarboxylase inhibitor, that is, a compound of Formula I is released, preferably 30 to 60 minutes prior to the release of dopamine. The laminated coating may be formed by use of a nonaqueous solution of glycerides or a water-insoluble polymer such as ethyl cellulose or cellulose acetate phthalate. Formulations wherein the dopamine is enteric coated by use of mixtures of shellacs and shellac derivatives and cellulose acetate phthalates may also be employed.

In the specific examples included hereinbelow illustrative examples of suitable pharmaceutical formulations are described.

The compounds of Formula I can be prepared by various procedures which will be described individually below:

The compounds of Formula I wherein $R_1$ is hydrogen; $R_2$ is hydroxy; and $R_4$ (as defined by X) is hydrogen; except those wherein the phenyl ring as defined by X contains both a methoxy and hydroxy group; can be prepared by the method depicted in the following reaction scheme:

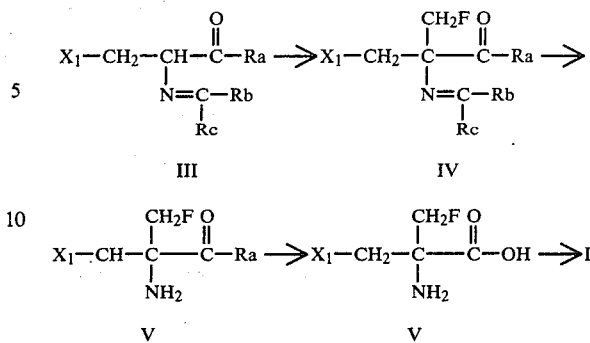

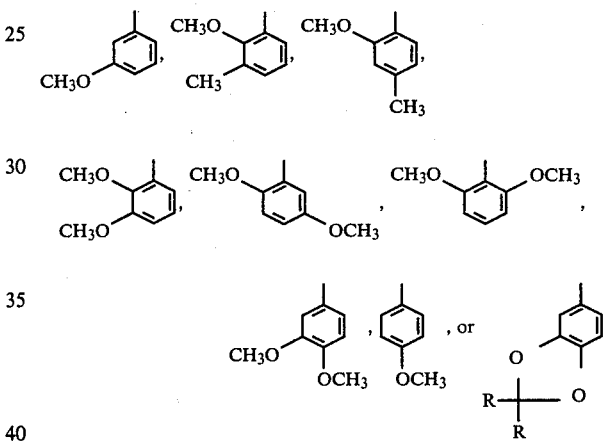

In the above depiction, Ra is $C_1$–$C_8$alkoxy; Rb is hydrogen, phenyl, $C_1$–$C_8$alkyl, methoxy, or ethoxy; Rc is phenyl or $C_1$–$C_8$alkyl; or Rb and Rc taken together form an alkylene group of from 5 to 7 carbon atoms (i.e. —$CH_2(CH_2)_mCH_2$—, where m is 3, 4 or 5); and $X_1$ is a methoxy-substituted phenyl group of the formula:

wherein R is hydrogen or methyl.

In carrying out the above-depicted method, in the first step, a Schiff base ester (III) is haloalkylated to introduce the α-halomethyl group (Y) by first treating the Schiff base ester with a strong base to generate a carbanion and then treating the carbanion with a suitable haloalkylating agent. Following the haloalkylation step, the Schiff base ester (IV) is hydrolyzed with acid, either in one step or stepwise, to give the final product (I).

Suitable strong bases which may be employed in the first step to form the carbanion intermediate are those which will abstract a proton from the carbon atom α to the carboxy group such as: an alkyl lithium (for example, butyl lithium or phenyl lithium), a lithium dialkylamide (for example, lithium diisopropylamide), lithium amide, potassium t-butylate, sodium amide, a metal hydride (for example, sodium hydride or potassium hydride), tertiary amines (for example triethylamine), lithium acetylide, or dilithium acetylide. Lithium acetylide, dilithium acetylide, sodium hydride and lithium diisopropylamide are preferred bases.

Suitable haloalkylating reagents for introducing the monofluoromethyl group are: chlorofluoromethane, bromofluoromethane, or fluoroiodomethane. The haloalkylating reagents are known in the art.

The haloalkylating reaction may be carried out in an aprotic solvent, for example, benzene, toluene, esters, such as tetrahydrofuran, dimethylsulfoxide or hexamethyl phosphortriamide. The reaction temperature may vary from about −120° C. to about 65° C., a preferred reaction temperature being about 40° C. The reaction time will vary from about ½ hour to 24 hours.

The hydrolysis of the alkylated Schiff base ester (IV) can be accomplished in one step under conditions capable of cleaving the

bond, the ester function (Ra), and the aromatic methoxy groups (as defined by $X_1$) concurrently, or it can be accomplished stepwise under conditions capable of selectively cleaving the hydrolyzable groups. In a two step method, the

bond is first cleaved and the ester and aromatic methoxy functions are then cleaved concurrently. In a three-step method, the three groups are each cleaved successively. Conditions for such selective transformations are well known in the art. In a one-step hydrolysis procedure the intermediate (IV) can be converted to the desired product (I) directly by treatment with hydrobromic acid, for 1 to 4 days at an elevated temperature, for example, about 80° to 125° C. In a stepwise procedure, the

bond of intermediate (IV) can be selectively hydrolyzed to the amino acid ester (V) by treatment with a dilute acid, such as hydrochloric acid for about 0.5 to 6 hours at 25° C. The ester function ($R_2$ is alkoxy) can be hydrolyzed selectively in the presence of an aromatic methoxy group to give the amino acid (VI) by treatment with a concentrated acid, such as hydrochloric acid or sulfuric acid, at a temperature of about 80° C. Finally the aromatic methoxy group of the amino acid (VI) can be cleaved to the desired product (I) by treatment with hydrobromic acid at an elevated temperature, for example about 80° to 125° C., for 1 to 4 days.

To facilitate purification, the

bond of any unalkylated starting material (III) which may be present in the reaction product can be selectively hydrolyzed in the presence of the

bond of the haloalkylated product (IV) by treatment with a stoichimetric amount of dilute hydrochloric acid or with a weak acid, such as acetic acid. The water soluble unalkylated salt of the amine thus formed can be separated from the haloalkylated Schiff base (IV) by conventional procedures. The Schiff base (IV), free of starting material (III), can then be hydrolyzed using the methods above-described to give the final product (I or II).

The step-wise hydrolysis procedure comprising the steps of hydrolyzing the unalkylated starting material (III) to separate it from the haloalkylated Schiff base (IV), selectively hydrolyzing the

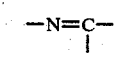

bond of the alkylated Schiff base (IV) to form the amino ester (V), and hydrolyzing the amino ester directly to the final product (I) is preferred.

The compounds of Formula I wherein $R_1$ is hydrogen, $R_2$ is hydroxy, and $R_4$, as defined by X, is hydrogen; except those wherein the phenyl ring, as defined by X, contain both a methoxy and hydroxy group; can be also prepared by the method depicted in the following reaction scheme:

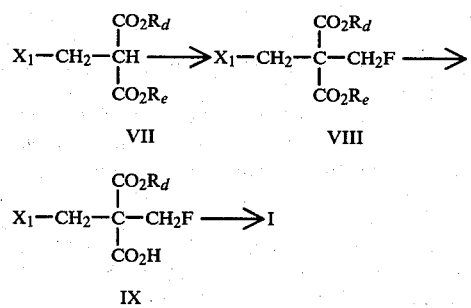

In the above scheme, $X_1$ has the meanings hereinbefore described, $R_d$ is $C_1$-$C_4$alkyl, and $R_e$ is t-butyl or benzyl. In carrying out the above-depicted method, a mixed malonic acid diester (VII) is haloalkylated to introduce the α-halomethyl group (Y) using the haloalkylation method above-described with reference to haloalkylation of the Schiff base (III). The haloalkylated diester is then hydrolyzed using trifluoroacetic acid, which selectivity removes the t-butyl group or using hydrobromic acid in acetic acid at room temperature which removes the benzyl group, to give the carboxylic acid (IX). Alternatively, the benzyl group can be removed by hydrogenolysis. The carboxylic acid intermediate (IX) can be converted to the desired amine by methods known in the art to be useful for converting a carboxyl group to a primary amino group. One method is by the Curtius reaction (see, for example, Organic Reactions, Vol. III, page 338) which proceeds via the corresponding acyl azide and isocyanate. In this procedure, the acid (IX) is transformed into the corresponding acid chloride by known methods, such as by reaction of the free acid with thionyl chloride or reaction of the corresponding sodium salt of the acid with oxalyl chloride. The acid chloride is next treated with sodium azide to form the corresponding acyl azide. The reaction forming the acyl azide is carried out in acetone at 0° C. to 40° C. for 1 to 12 hours. The acyl azide is isolated by conventional methods and is heated in a non-reactive solvent at 70° C. to 180° C. for 1 hour to 6 hours to afford the corresponding isocyanate by rearrangement. A preferred method is to heat the acyl azide in refluxing benzene for about 2 hours. Acid hydrolysis of the isocyanate, such as with 48% hydrobromic acid at 80°–125° C. for 1 to 4 days, yields the amino acid product. Under such conditions, the isocyanate function, the ester function ($R_d$), and the methoxyl groups (as defined by X) are hydrolyzed concurrently. The acyl azide can also be rearranged in an alcohol to form the corresponding carbamate which can be purified by chromatography.

To aid in purification, the isocyanate reaction product (formed by thermal rearrangements of the acyl azide) can be pretreated with 2–5 N hydrochloric acid at 0° to 40° C. for 1 to 6 hours, under which conditions the unalkylated isocyanate by-product is preferentially hydrolyzed to give the corresponding unalkylated amino acid which can be separated from the desired haloalkylated isocyanate by conventional methods.

Other methods for converting the acid (IX) to the desired product (I) are by means of the Schmidt reaction or the Hofmann Rearrangement. In the Schmidt reaction (see, for example, Organic Reactions, Vol. III, page 308), the acid is treated with hydrazoic acid in the presence of a strong mineral acid, such as sulfuric acid at 0° to 60° C. for 1 to 24 hours. In the Hofmann Rearrangement, (see for example Organic Reactions, Vol. III, page 268), the acid is converted first to the corresponding amide by conventional methods, and the amide is transformed to the amine via the corresponding N-haloamide and isocyanate. A preferred procedure entails the treatment of the amide with iodobenzene bis-(trisfluoroacetate) in acetonitrile-water (1:1 v/v) at room temperature (see Radhakrishna et al., J. Org. Chem. 44, 1746 (1979)).

The compounds of Formula I wherein $R_1$ is hydrogen, $R_2$ is hydroxyl, and $R_4$, as defined by X, is hydrogen; except those wherein the phenyl ring, as defined by X, contains both a hydroxy and a methoxy group; can be made by the procedure shown in the following reaction scheme:

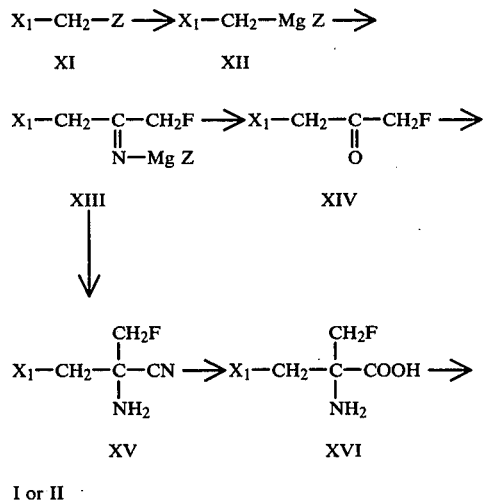

In the compounds of Formula XI to XVI as shown above, Z is a chlorine or bromine and $X_1$ is a methoxy-substituted phenyl group as hereinbefore defined with respect to Formula III.

In the above reaction sequence, a benzyl halide (XII) is added very slowly to magnesium in a suitable ether solvent, such as, tetrahydrofuran, diethylether or mixtures threof and the reaction is allowed to proceed for from 30 minutes to 24 hours at a temperature of from about $-20°$ C. to 70° C., preferably from about 25° C. to the boiling point of the solvent. At the beginning of the reaction a trace of methyliodide may be added. Also, if a methoxy group is present at the 2- or 4-position, the reaction is initiated in tetrahydrofuran.

To the thus formed Grignard reagent, is added fluoroacetonitrile at a ratio which can vary from 0.5 to 3, in an aprotic solvent, such as, tetrahydrofuran, diethylether, dioxane, benzene, dimethoxyethane, or dimethoxymethane or mixtures thereof. The temperature of the reaction will vary from $-20°$ C. to $-70°$ C., preferably from $-20°$ C. to $-25°$ C., and the reaction will vary from 10 minutes to 12 hours, preferably from 10 minutes to 1 hour. The thus formed ketimine salt (XIII) is hydrolyzed with acid to give the ketone (XIV). Acid hydrolysis may be achieved by pouring the ketimine salt onto water and concentrated hydrochloric acid, maintaining a strongly acidic medium. The ketone (XIV) can be isolated by conventional means, for example, by extraction with petroleum ether or pentane or hexane and then with ethers such as diethylether.

The ketone (XIV) can be converted to the amino nitrile (XV) under the conditions of the Strecker reaction by treatment with 1 to 10 equivalents of sodium cyanide and 1 to 10 equivalents of an ammonium salt, for example, ammonium chloride in either a basic medium using aqueous ammonium hydroxide (1 molar to concentrated) in a lower alcohol, such as, methanol or ethanol or a neutral medium using water and a lower alcohol. A reaction time of about one to about 7 days is employed.

An alternative procedure to prepare the amino nitrile (XV), employs the direct reaction of the fluoromethyl ketimine salt (XIII) with a cyanide salt (such as potassium or sodium cyanide) in the presence of two equivalents of an acid (such as ammonium chloride) in an aqueous or non-aqueous organic solvent at a temperature of about $-20°$ to 25° C. Using this procedure, the reaction for forming the amino nitrile (XV), is rapid. The direct reaction of the fluoromethyl ketimine salt with a cyanide salt and in the presence of an acid is the preferred method for making the aminonitrile (XV).

The aminonitrile (XV) can be hydrolyzed in one step or stepwise to give the corresponding amino acid. In a one-step method, the hydrolysis can be performed using hydrogen bromide at 80° to 125° C. for about 0.5 to 32 hours, under which conditions hydrolysis of the nitrile function is also accompanied by cleavage of any methoxy groups present in the phenyl ring. In a stepwise method, the aminonitrile (XV) is treated with a lower alcohol (e.g. methanol or ethanol) saturated with anhydrous hydrogen chloride for 1 to 64 hours, preferably 10 to 16 hours, at about 0° to 50° C., preferably 25° C., to give the corresponding amino acid amide, which is then hydrolyzed to the amino acid (XVI) by treatment with 50% aqueous sulfuric acid for about 2 to 6 hours at about 60° C. to 100° C., preferably 95° C. The sulfuric acid must be removed, such by reaction with barium hydroxide. Following formation of the α-amino acid, the aromatic methoxy group can be cleaved by treatment with concentrated hydrobromic acid at elevated temperatures (such as hereinbefore described) to give the final product (I).

It will also be appreciated that the fluoromethyl ketone (XIV) can be synthesized by other methods well known in the art of chemistry and the product can be used in the Strecker reaction as hereinbefore described.

When it is desired to prepare a compound of Formula I wherein $R_1$ is hydrogen, $R_2$ is hydroxyl, and the phenyl ring, as defined by X, contains both a free hydroxyl group ($R_4$ is hydrogen) and a methoxy group, the above-described synthetic procedures may be employed using a starting material (III, VII, or XI) wherein $X_1$ is a group of the formula:

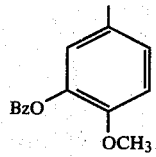

wherein Bz is the benzyl group. The aromatic benzyloxy group, as with the aromatic methoxy group, remains unreactive during each step of the syntheses up to the hydrolysis steps. The nitrile function is hydrolyzed and the benzyloxy functions is cleaved to a free hydroxy group under conditions which do not affect the methoxy group. Conditions for such transformations are known in the art.

The compounds of Formula I wherein $R_4$, as defined by X, is ($C_1$-$C_4$alkyl)carbonyl, benzoyl, or phenyl($C_1$-$C_8$alkylene)carbonyl can be prepared by treating the corresponding derivatives wherein $R_4$ is hydrogen with an acid anhydride of the formula

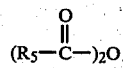

or an acid halide of the formula

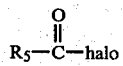

wherein halo is chlorine or bromine and $R_5$ is $C_1$-$C_4$alkyl, phenyl or phenyl($C_1$-$C_8$alkylene) in the presence of an organic base such as pyridine, quinoline or triethylamine, which base serves as the solvent, for about 1 to 24 hours at a temperature of about 25° C. to 100° C., with the proviso that prior to the reaction the α-amino group and optionally the carboxylic group of the hydroxy substituted starting material are protected with a suitable blocking group, respectively, such as, tert-butoxycarbonyl or benzyloxycarbonyl, or benzyl, which group is subsequently removed by treatment with acid, (for example, trifluoroacetic acid) or hydrogenolysis. The acid anhydride and acid halide reactants employed in this procedure are known in the art or can be prepared from the appropriate acids by procedures well known in the art.

The compounds of Formula I wherein $R_2$ is a $C_1$-$C_8$alkoxy group can be prepared by treating the corresponding derivatives, wherein $R_2$ is hydroxy, with an alcohol of the formula $R_6$—OH, wherein $R_6$ is a $C_1$-$C_8$alkyl, saturated with hydrogen chloride, at about 25° C. for from about 4 to 12 hours.

The compounds of Formula I wherein $R_2$ is amino, ($C_1$-$C_4$alkyl)amino or di($C_1$-$C_4$alkyl)amino can be prepared by reacting the acid halide, (for example, an acid chloride) of the corresponding compound wherein $R_2$ is hydroxy with ammonia or an appropriate ($C_1$-$C_4$alkyl)amine or di($C_1$-$C_4$alkyl)amine. The reaction is carried out in methylene chloride, chloroform, dimethylformamide, ethers such as tetrahydrofuran or dioxane, or benzene at about 25° C. for about 1 to 4 hours. Suitable amines are, for example, ammonia, or a compound which is a potential source of ammonia, for example, hexamethylenetetramine; primary amines, for example, methylamine, ethylamine, or n-propylamine; and secondary amines such as dimethylamine, diethylamine or di-n-butylamine.

The compounds of Formula I wherein $R_2$ is

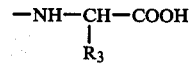

can be prepared by reacting the corresponding derivative, wherein $R_2$ is hydroxy, with a compound of the formula

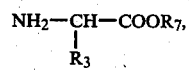

wherein $R_3$ has the meaning hereinbefore defined with respect to Formula I and $R_7$ is a $C_1$-$C_3$alkyl group (for example, methyl or ethyl) in the presence of a dehydrating agent such as dicyclohexylcarbodiimide.

It will be understood by those skilled in the art that when it is desired to prepare the compounds of Formula I wherein $R_2$ is amino, alkylamino, dialkylamino, or

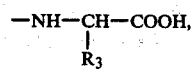

the free α-amino group in the starting amino propionic acid must be protected to avoid side reactions. Suitable α-amino protecting groups are well known in the art. Carbobenzyloxy and t-butoxycarbonyl are preferred. Moreover, when it is desired to prepare the alkylamido or dialkylamido compounds, any free hydroxyl group present in the phenyl ring of the starting material must also be protected, preferably using an alkylcarbonyl group. Following the reaction forming the amide bond, the α-amino protecting group is removed by treatment with acid, for example, hydrogen bromide in dioxane or hydrogenolysis. When appropriate, the hydroxy-protecting group is removed by base or acid hydrolysis.

The compounds of Formula I wherein $R_1$ is ($C_1$-$C_4$alkyl)carbonyl can be prepared by treating the corresponding derivatives wherein $R_1$ is hydrogen and $R_2$ is hydroxy with an acid halide of the formula

halo wherein halo is a halogen atom, for example, chlorine or bromine, and $R_8$ is $C_1$-$C_4$alkyl in water in the presence of a base such as sodium hydroxide or sodium borate at a temperature of from 0° C. to 25° C. for from ½ hour to 6 hours. These compounds may also be prepared from the ester derivative, that is, compounds of general Formula I, wherein $R_1$ is hydrogen and $R_2$ is a $C_1$-$C_8$alkoxy group, by treatment with the acid halide,

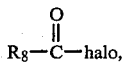

described above, in water, methylene chloride, chloroform or dimethyl acetamide in the presence of a base such as sodium hydroxide, potassium hydroxide or excess triethylamine at a temperature of from about 0° C. to 25° C. for from about ½ hour to 24 hours.

The compounds of general Formula I wherein $R_1$ is

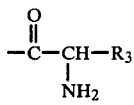

wherein $R_3$ is hydrogen, $C_1$–$C_4$alkyl, benzyl or p-hydroxybenzyl can be prepared by treating the corresponding derivative wherein $R_1$ is hydrogen and $R_2$ is a $C_1$–$C_8$alkoxy group with an acid of the formula

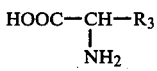

or an anhydride thereof (provided the α-amino group of the acid is protected with a suitable blocking group such as benzyloxycarbonyl or tert-butoxycarbonyl) in an ether, such as, tetrahydrofuran or dioxane, methylene chloride or chloroform, and in the presence of a dehydrating agent when the free acid is employed, at a temperature of from about 0° C. to 35° C. for about 1 to 12 hours followed by acid and base hydrolysis to cleave the ester function and to remove the α-amino protecting groups.

The individual optical isomers of the compounds of general Formula I wherein $R_1$ is H and $R_2$ is OH may be separated by known methods, such as by interaction with a chiral amine or acid. The individual optical isomers of compounds of Formula I wherein $R_1$ and $R_2$ are other than H and OH respectively may be obtained as described herein for the racemate only starting with the resolved amino acid.

The compounds of Formula III can be prepared by treating one equivalent of a glycinate of the formula

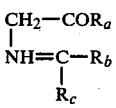   XVII wherein $R_a$, $R_b$ and $R_c$ have the meanings defined with respect to Formula III with one equivalent of a strong base such as an alkyl lithium (for example, butyl lithium), phenyl lithium, a lithium di-alkylamide (for example, lithium diisopropylamide), lithium amide, potassium t-butylate, sodium amide, a metal hydride (for example, sodium hydride) or a tertiary amine (for example triethylamine), lithium acetylide, or dilithium acetylide followed by treatment with an alkylating reagent of the following formula

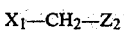   XVIII wherein $X_1$ has the meaning hereinbefore defined with respect to Formula III and $Z_2$ is a halogen atom, for example, chlorine or bromine. The alkylation reaction may be carried out in an aprotic solvent, for example, benzene, ethers, tetrahydrofuran, dimethylsulfoxide or hexamethylphosphortriamide. The reaction time varies from about ½ hour to 24 hours and the temperature varies from about $-120°$ C. to 25° C.

The compounds of general Formula XVII can be prepared by treating an appropriate alkyl glycinate with a carbonyl bearing compound to form a Schiff's base in a generally known manner, specifically, (a) when $R_b$ is hydrogen, by treating the appropriate amino acid ester with benzaldehyde or an alkanal having from 1 to 9 carbon atoms being straight or branched, for example, 1-propanal, 1-butanal, 2,2-dimethylpropan-1-al or 2,2-diethylbutan-1-al, (b) when $R_b$ is phenyl by treating the appropriate amino acid ester with benzophenone or phenyl alkyl ketone wherein the alkyl moiety has from 1 to 8 carbon atoms and is straight or branched, for example, phenyl methyl ketone, phenyl ethyl ketone, phenyl isopropyl ketone, phenyl n-butyl ketone or phenyl tert-butyl ketone, and (c) when $R_b$ is a straight or branched alkyl group having from 1 to 8 carbon atoms, treating the appropriate amino acid ester with a phenyl alkyl ketone as described above with a dialkyl ketone wherein each alkyl moiety has from 1 to 8 carbon atoms and is straight or branched, for example, dimethyl isopropyl ketone, di-n-butyl ketone or methyl tert-butyl ketone. The carbonyl bearing compounds are known in the art or may be prepared by procedures well known in the art.

When $R_b$ is methoxy or ethoxy in compounds of Formula XVII, an appropriate alkyl glycinate is reacted with benzoyl halide (for example, benzoyl chloride) or an alkanoic acid halide (for example, the chloride) wherein the alkanoic acid has from 1 to 9 carbon atoms and is straight or branched (for example, acetyl chloride, propionyl chloride, butyryl chloride, t-butyryl chloride, 2,2-diethylbutyric acid chloride or valeryl chloride) at 0° C. in ethers, methylenechloride, dimethylformamide, dimethylacetamide, or chlorobenzene in the presence of an organic base such as triethylamine or pyridine, after which the reaction mixture is allowed to warm to about 25° C. for 1 hour. The resulting amide derivative is combined with an alkylating reagent, such as, methylfluorosulfonate, dimethylsulfate, methyliodide, methyl p-toluenesulfonate or trimethyloxonium hexafluorophosphate when $R_b$ is methoxy, or triethyloxonium tetrafluoroborate when $R_b$ is ethoxy, at about 25° C. in a chlorinated hydrocarbon solvent, such as, methylene chloride, chlorobenzene or chloroform, and the reaction mixture is refluxed for about 12 to 20 hours. The mixture is then cooled to about 25° C. and an organic base, such as, triethylamine or pyridine is added after which the solution is extracted with brine and the product isolated.

When in the compounds of Formula XVII $R_b$ and $R_c$ together form an alkylene group of from 5 to 7 carbon atoms said amino acid ester derivatives are obtained by treating the amino acid ester with a cyclic alkanone selected from cyclopentanone, cyclohexanone and cycloheptanone to form a Schiff's base by procedures generally known in the art.

The alkyl glycinates are obtained by treating glycine with an alcohol of the formula $R_aH$, wherein $R_a$ has the meaning hereinbefore defined with respect to Formula III, saturated with HCl gas at about 25° C. for about 12 to 36 hours, or the compounds may be obtained from commercial sources.

The compounds of Formula XVIII are known in the art or may be prepared from the corresponding appropriately substituted benzoic acid or benzaldehyde derivatives which are known in the art. For example, the benzylhalides of Formula XVIII may be prepared from the corresponding benzaldehyde by reduction with sodium borohydride or lithium aluminium hydride or by catalytic reduction, or from the corresponding benzoic acid ester by reduction with lithium aluminium hydride or borane, or reduction of the corresponding benzoic acid derivative with lithium hydride and treating the thus formed benzyl alcohol derivative with a halogenating agent, for example, thionyl chloride, phosphorus oxychloride, phosphorus trichloride, phosphorus tribromide or phosphorus pentachloride.

Certain compounds of general Formula III may be obtained directly from the appropriate amino acid by converting said acids to an appropriate ester, and then protecting the α-amino group by the general procedures described hereinabove for protecting the alkyl glycinate amino group. For example, the amino protected ester derivative of tyrosine may be obtained in such a manner. This procedure is not preferred to prepare compounds of Formula III wherein the aromatic ring contains a hydroxy group in the meta-position however.

The compounds of Formula VII are prepared by alkylating a mixed malonic ester of the formula:

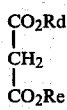 XIX wherein Rd and Re have the meaning defined with respect to Formula VII, with the alkylating agent of Formula XVIII, wherein $X_1$ and $Z_2$ have the meanings hereabove defined with respect to Formula XVIII. The alkylation reaction is carried out using the same conditions and reagents as hereinbefore discussed for the preparation of the compounds of Formula III. The compounds of Formula XIX are either known compounds or can be prepared by methods known in the art.

The methods and processes of this invention are further illustrated in the following Examples:

EXAMPLE 1

2-Amino-2-fluoromethyl-3-(3,4-dihydroxyphenyl)propionic acid

A. 1-Fluoro-3-(3,4-dimethoxyphenyl)-2-propanone

Under an atmosphere of nitrogen, 3,4-dimethoxybenzyl chloride (12.20 g) in tetrahydrofuran (THF) (80 ml) is added slowly (within 1 hour) to magnesium turnings (3.0 g) in THF (50 ml). During the addition, the flask is immersed in a bath containing water at room temperature. Stirring is continued for one hour. The Grignard reagent is then separated from the excess magnesium and transferred into a second flask (under nitrogen) cooled to −20° C. Fluoroacetonitrile (4.0 g) in THF (25 ml) is added from a dropping funnel at such a rate that the internal temperature is maintained between −25° and −20°. After the addition, stirring is continued for one hour at −20°, and the solution is poured on a mixture of ice (200 g), water (240 ml), and concentrated hydrochloric acid (120 ml), and extracted with petroleum ether (2×100 ml) and diethyl ether (4×100 ml). Drying ($Na_2SO_4$) and evaporation of the ethereal extracts yields 4.53 g (33%) of pure ketone, b.p. 100° C./0.35 mm Hg.

B.

2-Amino-2-fluoromethyl-3-(3,4-dimethoxyphenyl)propionitrile

To a suspension of 1-fluoro-3-(3,4-dimethoxyphenyl)-2-propanone (31.5 g, 0.149 mol) and ammonium chloride (9.57 g, 0.179 mol) in a solution of 28% aqueous ammonia (170 ml) is added sodium cyanide (8.77 g, 0.179 mol). The reaction mixture is stirred at room temperature under nitrogen for 20 hours. The solid which separates is removed by filtration on sintered glass, and then washed with 28% aqueous ammonia (50 ml). The solid is dissolved in ether (1.3 l) and the solution is washed with water, then with brine, dried ($MgSO_4$), and filtered. Upon concentration of the solvent, 2-amino-2-fluoromethyl-3-(3,4-dimethoxyphenyl)-propionitrile crystallizes (21.8 g), m.p. 76° C.

C.

2-Amino-2-fluoromethyl-3-(3,4-dihydroxyphenyl)propionic acid

A solution of 2-amino-2-fluoromethyl-3-(3,4-dimethoxyphenyl)propionitrile (20.7 g, 0.086 mol) in 47% aqueous hydrobromic acid (300 ml) is heated under nitrogen at 100° C. for 32 hours. Concentration of the solvent under reduced pressure leaves a residue which is dissolved in isopropanol (300 ml). The solution is aged for 12 hours at 4° C. The ammonium bromide which separates is filtered and washed with isopropanol (3×40 ml). The filtrate is neutralized with triethylamine (16 g) in isopropanol until the pH of the solution reaches 4.5–5. The precipitate which forms is collected and washed extensively with chloroform. The residue (19.4 g) is dissolved in water (500 ml) and treated with charcoal. Upon concentration the product crystallizes (13 g). From the mother liquor, a second batch (1.2 g) of 2-amino-2-fluoromethyl-3-(3,4-dihydroxyphenyl)propionic acid is obtained, m.p. 230° C.

EXAMPLE 2

2-Amino-2-fluoromethyl-3-(2,3-dihydroxyphenyl)propionic acid

A. 2,3-Dimethoxybenzyl chloride

Thionyl chloride (288 g) is added over 1.5 hour to a stirred solution of 2,3-dimethoxybenzyl alcohol (400 g) and 2,6-lutidine in methylene chloride (2 l). The reaction mixture is then stirred for 30 minutes after which it is washed with 2 N hydrochloric acid (7×1 l) and then with water. The organic layer is separated, dried ($MgSO_4$) and evaporated to give a residue, which upon distillation yields 3,4-dimethoxybenzyl chloride (375 g), b.p. 145°–150° C. at 20–25 nm (waterpump vacuum). The material solidifies on standing.

B.

2-Amino-2-fluoromethyl-3-(2,3-dimethoxyphenyl)propionitrile

Ethyl bromide (1 ml) is added to magnesium turnings (48 g) and magnesium powder (48 g) covered with tetrahydrofuran (THF) (800 ml). 2,3-Dimethoxybenzyl chloride (336 g) in THF (2000 ml) is then added over 2.5 hours while the reaction mixture is maintained at 20° C. by means of a water bath. After the addition, the mixture is stirred for one additional hour and excess magnesium is removed by decantation. The Grignard reagent thus obtained is cooled to −35° C. and fluoroacetonitrile (105 g) in THF (600 ml) is added at −40° C. to −30° C. Cooling is continued for one hour. The reaction mixture is poured into a solution of sodium cyanide (175 g) and ammonium chloride (275 g) in water (4 l) at 10° C. After the mixture is stirred for 30 minutes, the organic phase is separated. The water phase is saturated with sodium chloride (250 g) and is washed with ether (3×1 l). The combined organic phases are dried (MgSO4), filtered, and evaporated to dryness. The residue, dissolved in ether (2 l), is extracted with 10% hydrochloric acid (4×250 ml) and the acid phases are combined, extracted with diethyl ether, and made basic with conc. ammonium hydroxide. The oil, which separates, is taken up into diethyl ether (1 l), and the solution is dried (MgSO4), filtered, and evaporated to give the propionitrile product (110 g) as a brown oil.

C.
2-Amino-2-fluoromethyl-3-(2,3-dihydroxyphenyl)propionic acid

2-Amino-2-fluoromethyl-2-(2,3-dimethoxyphenyl)-propionitrile (100 g) and 48% hydrobromic acid (500 ml) are heated under reflux overnight. The hot solution is treated with charcoal (5 g), filtered, and evaporated to dryness over water-pump vacuum. The residue is treated with water (250 ml) and the mixture taken to dryness. This procedure is repeated. The residue is taken up in hot isopropanol (500 ml). After filtration of the insoluble ammonium bromide, the solution is concentrated (to about 400 ml). Trimethylamine is then added to adjust the pH to 5, and diethylether (1 l) is added. A solid which separates is collected and washed with chloroform (4×250 ml). The remaining solid is dried and taken up in boiling water (1 l). Charcoal is added. After removal of the charcoal by filtration, the mixture is concentrated (to about 400 ml) and cooled. The light brown solid which separates is collected and washed with cold isopropanol and diethylether. Recrystallization three times from water, gives the title product (24 g), m.p. 224° C. (dec).

EXAMPLE 3
2-Amino-2-fluoromethyl-3-(2,5-dihydroxyphenyl)propionic acid

A. Fluoroacetonitrile

A stirred mixture of phosphorous pentoxide (200 g), fluoroacetamide (150 g) and hexamethylphosphoramide (500 ml), in a 2 l reactor fitted with a simple distillation head, a distillation condenser and a receiver cooled in a mixture of solid carbon dioxide/acetone, is slowly heated to 50° C. under a pressure of 90 mm Hg. At this temperature a vigorous reaction commences and fluoroacetonitrile begins to distil at 38° C.

After the vigorous reaction has subsided (~3 minutes) the temperature of the oil bath is slowly raised to 140° C. and the remaining fluoroacetonitrile is collected at 38°–50° C. The fluoroacetonitrile (111 g) is obtained as a colorless liquid. An NMR analysis shows that it contains traces of hexamethyl phosphoramide which can be removed, if desired, by a redistillation, but its presence is not detrimental for the subsequent Grignard reaction.

B. 2,5 Dimethoxybenzyl chloride

Thionyl chloride (108 g) is slowly added during 1 hour to a stirred mixture of 2,5-dimethoxybenzyl alcohol (150 g), 2,4,6-collidine (108 g), and methylene chloride (750 ml) at room temperature. The reaction is slightly exothermic. After stirring for another 30 minutes, the mixture is washed with hydrochloric acid (2 N) and water and then dried (MgSO4). Evaporation gives a residue of 2,5-dimethoxybenzyl chloride which crystallizes (127 g).

Analysis for C9H11Cl: Calculated C, 57.92%, H, 5.94; Found C, 57.93; H, 5.94.

C.
2-Amino-2-fluoromethyl-3(2,5-dimethoxyphenyl)propionitrile

Ethyl bromide (2 ml) is added to magnesium turnings (25 g, 1 mol) covered with anhydrous tetrahydrofuran at room temperature under nitrogen. When the reaction has subsided, 2,5-dimethoxybenzyl chloride (102.5 g, 0.55 mol) in anhydrous tetrahydrofuran (200 ml) is slowly added at such a rate to cause a gentle reflux. After stirring for a further hour, the Grignard solution is decanted from the excess magnesium (11.7 g), cooled to −35° C., and treated with a solution of fluoroacetonitrile (33.6 g, 0.59 mol) in anhydrous tetrahydrofuran (200 ml) by dropwise addition, a nitrogen atmosphere being maintained throughout. The mixture is stirred for a further hour at −35° C. and then poured into a stirred solution of sodium cyanide (55 g) and ammonium chloride (88 g) in water (1 l) at 10° C. The mixture is stirred for 30 minutes. The organic phase is then separated. The aqueous phase is saturated with sodium chloride and extracted with ether (2×). The combined organic phases are charcoaled, dried (MgSO4), filtered, and evaporated to give an oil (112 g). A solution of the oil in anhydrous diethylether is treated with ethereal hydrogen chloride and the precipitated oil is crystallized by trituration. The solid is filtered and washed well with ether to give crude 2-amino-2-fluoromethyl-3(2,5-dimethoxyphenyl)propionitrile as the hydrochloride (80 g).

D.
2-Amino-2-fluoromethyl-3(2,5-dimethoxyphenyl)propionamide

The amino nitrile prepared in step C (80 g) is dissolved in the minimum of methanol and treated with an equal volume of methanol saturated with hydrogen chloride at 0° C. The mixture is allowed to stand in a refrigerator overnight and then evaporated. The residue is crystallized by trituration under ether to give 2-amino-2-fluoromethyl-3(2,5-dimethoxyphenyl)propionamide as the hydrochloride (68 g).

E.
2-Amino-2-fluoromethyl-3(2,5-dihydroxyphenyl)propionic acid

A mixture of the amide prepared in step D (68 g) and 47% hydrobromic acid (250 ml) is refluxed for 1 night under nitrogen. The hot solution is treated with charcoal, filtered, and evaporated to dryness. Dioxan is added to the residue and evaporated to remove the last traces of water. Dioxan treatment is repeated once. A solution of the residue in isopropanol is filtered to remove ammonium bromide and concentrated to about 250 ml. The pH of the solution is adjusted to 5 by the addition of triethylamine in isopropanol. Anhydrous ether (~1 l) is added, the mixture is filtered, and the solid so obtained is washed with chloroform to remove triethylamine hydrobromide.

The solid is dissolved in water (1 l at 100°) and the solution is charcoaled and evaporated to about 500 ml where 2-amino-2-fluoromethyl-3-(2,5-dihydroxyphenyl)propionic acid begins to crystallize as the dihydrate (21 g). A further 10 g is obtained by concentration of the mother liquors, m.p. 212° C.

EXAMPLE 4

2-Amino-2-fluoromethyl-3-(2-hydroxy-3-methylphenyl)propionic acid

A.

2-Amino-2-fluoromethyl-3-(2-methoxy-3-methyl)phenyl propionitrile

All manipulations are carried out under an atmosphere of nitrogen.

A solution of ethylene dichloride (10.59 g, 0.107 mol) in anhydrous tetrahydrofuran (THF) (150 ml) is slowly added to a stirred mixture of magnesium turnings (2.59, 0.107 mol) and anhydrous THF (50 ml). The vigorous exothermic reaction is controlled by cooling with ice-cold water. The reaction is finally warmed at 30° C. to dissolve all the magnesium and the solution so obtained is added to a freshly prepared solution of sodium (4.9 g, 0.214 mol) in a mixture of naphthalene (28.2 g, 0.22 mol) and anhydrous tetrahydrofuran (200 ml). An immediate fine black suspension of magnesium is formed.

Magnesium turnings (2.5 g, 0.107 mol) are added to the above suspension to maintain an excess of magnesium, and the stirred mixture cooled to −20° C. A solution of 2-methoxy-3-methylbenzyl chloride (18.3 g, 0.107 mol) in THF (50 ml) is added during an hour, the black color of the mixture disappearing at the end of the addition. The solution is decanted from the excess magnesium and treated with a solution of fluoroacetonitrile (6.3 g, 0.107 mol) in anhydrous tetrahydrofuran (50 ml) at −20° C. by dropwise addition during 30 minutes. The mixture is stirred for a further hour at −20° C. and poured into a stirred aqueous solution of a mixture of sodium cyanide (10.49 g, 0.214 mol) and ammonium chloride (17.2 g, 0.32 mol).

After half an hour, the organic layer is separated using diethyl ether, dried, and concentrated to ⅓ volume. Ethereal hydrogen chloride is added and the mixture is allowed to crystallize. The crystals of 2-amino-2-fluoromethyl-3-(2-methoxy-3-methylphenyl)propionitrile, hydrochloride (m.p. 128° C.) are filtered off and recrystallized from acetonitrile (8 g).

B.

2-Amino-2-fluoromethyl-3-(2-methoxy-3-methylphenyl)propionamide

A solution of 2-amino-2-fluoromethyl-3-(2-methoxy-3-methylphenyl)propionitrile hydrochloride (5.2 g) in methanol saturated with hydrogen chloride (100 ml) is allowed to stand for 64 hours in a refrigerator. The methanol is evaporated, the residue is dissolved in water, and the solution basified by the addition of aqueous potassium carbonate. The organic material (4.8 g) is isolated by extraction with dichloromethane. The syrup is purified first by column chromatography using silica and a mixture of chloroform 93% and acetone 7% eluant, and finally by crystallization from benzene to give crystals of 2-amino-2-fluoromethyl 3(2-methoxy-3-methylphenyl)propionamide, m.p. 118° C. (3.5 g).

C.

2-Amino-2-fluoromethyl-3-(3-hydroxy-3-methylphenyl)propionic acid

A solution of 2-amino-2-fluoromethyl-3-(2-methoxy-3-methylphenyl)propionamide (1.5 g) in 48% hydrobromic acid is refluxed overnight, the acid evaporated, and the residue dissolved in isopropanol. After removing the ammonium bromide by filtration, the pH of the solution is adjusted to 5 by the addition of triethylamine. The crystals which separate are filtered, washed well with chloroform, and dissolved in water. The aqueous solution is evaporated and the residue crystallized from ethanol to give 2-amino-2-fluoromethyl-3-(2-hydroxy-3-methylphenyl)propionic acid, as the semi-hydrate, m.p. 168° C.

EXAMPLE 5

2-Amino-2-fluoromethyl-3-(3-hydroxy-4-methoxyphenyl)propionic acid

A.

2-Amino-2-fluoromethyl-3-(3-benzyloxy-4-methoxyphenyl)propionitrile

Under an atmosphere of nitrogen, 3-benzyloxy-4-methoxybenzyl magnesium chloride is prepared from 3-benzyloxy-4-methoxybenzylchloride (C. Schöpf and L. Winterhalder, Ann. 544, 62 (1940) (22.0 g, 84 mmol) and magnesium turnings (4.1 g) in tetrahydrofuran (THF) (100 ml) at room temperature (about 2 hours). After cooling to −30° C., a solution of fluoroacetonitrile (4.94 g) in THF (40 ml) is added dropwise, maintaining the temperature between −30° C. and −40° C. Stirring is continued at this temperature for another 30 minutes, then the mixture is poured into a solution of sodium cyanide (12.3 g) and ammonium chloride (17.9 g) in water (150 ml), previously cooled with ice. After stirring for 30 minutes, the mixture is saturated with sodium chloride whereupon the phases separate. After extracting the aqueous phase two more times with diethyl ether, the combined THF and ether phases are dried (Na$_2$SO$_4$) and evaporated to give the crude aminonitrile (25.9 g) as a brown oil. The oil is dissolved in ether and treated with HCl gas to prepare the hydrochloride as an oil. This oil is recrystallized twice from ethanol/ether to give 2-fluoromethyl-2-amino-3-(3'-benzyloxy-4'-methoxyphenyl)propionitrile as the hydrochloride as a slightly colored solid; NMR (CD$_3$OC): 3.47 ppm (3H, s), 4.32 ppm (2H, d, J$_{H-F}$=46 Hz), 4.73 ppm (2H, s), 6.60 ppm (3H, m), 6.97 ppm (5H, m).

B.

2-Amino-2-fluoromethyl-3-(3-hydroxy-4-methoxyphenyl)propionic acid

A solution of 2-amino-2-fluoromethyl-3-(3-benzyloxy-4-methoxyphenyl)propionitrile (0.7 g) in absolute methanol saturated with dry hydrogen chloride (50 ml) is heated at reflux for 12 hours. The methanol is evaporated and the residue dissolved in trifluoroacetic acid (10 ml). The mixture is heated at reflux temperature for 2 hours. Water (4 ml) is then added, and reflux continues overnight. The residue obtained upon evaporation under reduced pressure is passed through Amberlite 120 H+ ion exchange resin column. The ninhydrin positive fractions are pooled and concentrated. The residue is crystallized from water-methanol-ether to afford the desired product.

EXAMPLE 6

Methyl 2-amino-2-fluoromethyl-3-(4-hydroxyphenyl)propionate

A. 2-Amino-2-fluoromethyl-3-(4-methoxyphenyl)propionitrile

Under nitrogen, 4-methoxybenzylmagnesium chloride is prepared by adding 4-methoxybenzyl chloride (160 g) in tetrahydrofuran (THF) (800 ml) to magnesium turnings (50 g) and THF (400 ml) within about 2 hours. The reaction is initiated by the addition of a few drops of methyliodide, and the reaction flask is cooled by a bath containing water of room temperature. Stirring is continued for an additional ½ hour, and the solution is decanted from the excess of magnesium, transferred to a second flask and cooled to $-30°$ C. to $-40°$ C. Fluoroacetonitrile (58 g) in THF (250 ml) is added dropwise within 40 minutes, keeping the temperature (internal) between $-30°$ C. and $-40°$ C. After the addition, stirring is continued for 10 minutes at the same temperature then the reaction mixture is poured into a stirred solution of sodium cyanide (100 g) and ammonium chloride (100 g) in water (2 l) and stirred for 1 hour at room temperature. Sodium chloride (400 g) is added to separate the phases. The THF layer (upper phase) is removed, and the aqueous layer is extracted with diethyl ether $(3 \times 1\text{ l})$. After drying ($Na_2SO_4$) the THF solution and the ethereal extracts are stripped to give 200 g of crude product. Treatment of a solution of the crude nitrile in diethyl ether (3 l) with HCl gas precipitates the hydrochloride which is recrystallized from ethanol/ether (120 g).

B. 2-Amino-2-fluoromethyl-3-(4-hydroxyphenyl)propionic acid

Under nitrogen, 2-amino-2-fluoromethyl-3-(4-methoxyphenyl)-propionitrile, hydrochloride (30 g) and conc. hydrobromic acid (500 μl) are heated at 90° C. for 30 hours. After evaporation, the residue is dissolved in water, and aqueous ammonia is added until pH 5.5 The precipitate is collected, dried and washed several times carefully with acetone. The washed precipitate is dissolved in 2 N hydrochloric acid, treated with charcoal, and reprecipitated by addition of ammonia (pH 5.5). Reprecipitation in the same manner gives 2-amino-2-fluoromethyl-3-(4-hydroxyphenyl)propionic acid (16.6 g), mp 239° C. (dec.).

Anal: Calcd for $C_{10}H_{12}FNO_3$: C, 56.33, H, 5.67, N, 6.57. Found: C, 56.34, H, 5.73, N, 6.42.

C. Methyl 2-amino-2-fluoromethyl-3-(4-hydroxyphenyl)propionate

With ice cooling, a suspension of 2-amino-2-fluoromethyl-3-(4-hydroxyphenyl)propionic acid (10.0 g) in absolute methanol (400 ml, dried over magnesium) is saturated with HCl gas. After heating at 90° C. overnight, the solvent is removed under reduced pressure, and the residue is dried for 3 hours under the vacuum of an oil pump. After dissolving in absolute methanol (400 ml) and saturating with HCl gas, the mixture is heated at 90° C. overnight again. After evaporation of the solvent, the residue is dissolved in water and a solution of sodium carbonate is added with stirring until pH~10. The suspension is extracted 3 times with ether; the combined ether extracts are filtered, washed carefully with water, dried ($Na_2SO_4$) and evaporated to give pure methyl 2-amino-2-fluoromethyl-3-(4-hydroxyphenyl)propionate (7.5 g, 70%) as white crystals, m.p. 130° C.; NMR ($CD_3OD$): δ2.77 (2H, AB, $J_{AB}=14$ Hz), 3.70 (3H, s), 4.50 (2H, ABX, $J_{AB}=9$ Hz, $J_{AX}=J_{BX}=J_{H-F}=46$ Hz), 6.87 (4H, $A_2B_2$ with additional fine splitting, $J_{AB}=9$ Hz).

Anal: Calcd for $C_{11}H_{14}FNO_3$: C, 58.14; H, 6.21; N, 6.16. Found: C, 58.32; H, 6.34; N, 6.18.

EXAMPLE 7

2-Amino-2-fluoromethyl-3-(2,3-dihydroxyphenyl)propionic acid

A. 1-Fluoro-3-(2,3-dimethoxyphenyl)-2-propanone

1-Fluoro-3-(2,3-dimethoxyphenyl)-2-propanone is prepared via 2,3-dimethoxybenzyl chloride and fluoroacetonitrile by the method described in step A of Example 4.

B. 2-Amino-2-fluoromethyl-3-(2,3-dimethoxyphenyl)propionitrile

A mixture of 1-fluoro-3-(2,3-dimethoxyphenyl)-2-propanone (4.07 g, 19.2 mmol), ammonium chloride (2.05 g, 38 mmol), and 28% aqueous ammonia (25.4 ml) is treated with sodium cyanide (1.88 g, 38.4 mmol) in isopropanol (30 ml). The mixture is stirred at room temperature for 96 hours after which the solvent is evaporated in vacuo. The residue is taken up in water, and the water mixture is extracted with diethyl ether. The ethereal extract is washed with a saturated aqueous solution of sodium chloride and then dried ($MgSO_4$). Filtration and removal of the solvent in vacuo affords the free aminonitrile as a brown oil. The 2-amino-2-fluoromethyl-3-(2,3-dimethoxyphenyl)propionitrile is precipitated in ether as the hydrochloride by dropwise addition of a saturated solution of hydrogen chloride in ether to an ethereal solution of the free aminonitrile. The product is recrystallized from ethanol ether.

C. 2-Amino-2-fluoromethyl-3-(2,3-dihydroxyphenyl)propionic acid

A solution of 2-amino-2-fluoromethyl-3-(2,3-dimethoxyphenyl)propionitrile, hydrochloride (0.900 g, 3.2 mmol) in 47% aqueous hydrobromic acid (30 ml) is heated under nitrogen at 100° C. for 18 hours. The solution is evaporated to dryness under reduced pressure, the residue is dissolved in water, and the solution decolorized using active charcoal. Filtration and evaporation of the solvent in vacuo yields a colorless oil. The oil is dissolved in isopropanol (20 ml), ammonium bromide is filtered off, and the solvent is evaporated. Triethylamine is added to a solution of the residue in water until the pH reaches ~5. The precipitated solid is filtered off, dissolved in water, and decolorized using active charcoal. Filtration and evaporation of the solvent in vacuo yields the title product which is recrystallized from water and ethanol, m.p. 223° C.; NMR ($D_2O/DCl$): 3.27 ppm (m, 2H); 4.87 ppm (2AB, $J_{AB}=11$ Hz, $J_{HF}=45$ Hz, 2H); 6.62–7.00 ppm (m, 3H).

EXAMPLE 8

2-Amino-2-fluoromethyl-3-(4-hydroxyphenyl)propionic acid

A. 4-Methoxybenzyl triphenylphosphonium bromide

A mixture of 4-methoxybenzyl bromide (143 g, 0.71 mol), triphenyl phosphine (189.8 g; 0.72 mol) and benzene (400 ml) is refluxed for 48 hours. The solid which separates is collected and recrystallized from isopropanol to give crystals of 4-methoxybenzyl triphenylphosphonium bromide containing 1 mol of isopropanol of crystallization (297 g). Azeotropic distillation with toluene gives crystals of 4-methoxybenzyl triphenylphosphonium bromide containing 1/5 mol of isopropanol.

B. 2-Ethoxy-1-fluoro-3-(4-methoxyphenyl)prop-2-ene

To a suspension of finely divided 4-methoxybenzyl triphenylphosphonium bromide (containing 1/5 mol isopropanol) (240 g, 0.5 mol) in anhydrous benzene (500 ml) is added a solution of sodium hexamethyldisilazane (0.5 mol) in anhydrous benzene (1.3 l). The mixture is heated under reflux for 2 hours. The cooled solution is filtered under nitrogen and treated with ethyl fluoroacetate (50 ml, ~0.5 mol), the total volume of the solution being adjusted to 3 l by the addition of anhydrous benzene. The stirred mixture is refluxed under nitrogen until the deep red color virtually disappears (9 days).

The benzene is removed by evaporation under slightly reduced pressure, the residue is dissolved in anhydrous diethyl ether, and an equal volume of pentane is added. The solid triphenylphosphine oxide is removed by filtration, and the filtrate is evaporated under reduced pressure. Distillation of the residue affords a liquid, b.p. 45°–9°/0.05 mm (11 g), later identified to be p-methoxytoluene by NMR analysis, and 2-ethoxy-1-fluoro-3-(4-methoxyphenyl)prop-2-ene (35 g), b.p. 111°–120° C. /0.05 nm; NMR (CDCl$_3$): 6.76–7.72 ppm (4H, m), 5.68 ppm (1H, d, J=6 Hz), 4.96 ppm (2H, d, J=48 Hz), 4.08 ppm (2H, q, J=7 Hz), 3.82 ppm (3H, s), 1.4 ppm (3H, t, J=7 Hz).

C. 1-Fluoro-3-(4-methoxyphenyl)-2-propanone

2-Ethoxy-1-fluoro-3-(4-methoxyphenyl)prop-2-ene (5 g, 0.024 mol) is stirred with a saturated solution of hydrogen chloride in diethyl ether (40 ml) overnight. Water (18 ml) is added and the stirring is continued for another 3 hours. The ether layer is separated, washed with water, dried (MgSO$_4$), and filtered. Concentration of the solvent affords 1-fluoro-3-(4-methoxyphenyl)-2-propanone (4.2 g); NMR (CDCl$_3$): 6.7–7.3 ppm (4H, m), 4.8 ppm (2H, J=48 Hz), 3.7–3.9 ppm (5H, m).

D. 2-Amino-2-fluoromethyl-3-(4-methoxyphenyl)propionitrile

A mixture of 1-fluoro-3-(4-methoxyphenyl)-2-propanone (4.1 g, 0.0225 mol), ammonium chloride (1.5 g) and 28% aqueous ammonia (27 ml) is treated with sodium cyanide (1.4 g), and the mixture is stirred at room temperature overnight under nitrogen. The oil which separates is removed and extracted with diethyl ether, and the ethereal extract is washed with ammonia, dried (MgSO$_4$), and filtered. Evaporation of the ether leaves an oily residue which is washed with pentane by decantation. An NMR analysis of the oily residue (4 g) shows that it consists mainly of the required 2-amino-2-fluoromethyl-3-(4-methoxyphenyl)propionitrile.

E. 2-Amino-2-fluoromethyl-3-(4-hydroxyphenyl)propionic acid

A solution of the crude 2-amino-2-fluoromethyl-3-(4-methoxyphenyl)propionitrile (4 g) in 47% aqueous hydrobromic acid (80 ml) is heated under nitrogen at 100° for 30 hours. The solution is evaporated to dryness under reduced pressure, the residue is dissolved in isopropanol, the ammonium bromide is removed by filtration, and isopropanol is removed by evaporation. Triethylamine is added to a solution of the residue in water (50 ml) until the pH reaches 4.7. The precipitated solid is collected and recrystallized from water using charcoal to give crystals of the title product (1.4 g), m.p. 243° C.

EXAMPLE 9

2-Amino-2-fluoromethyl-3-(3-hydroxyphenyl)propionic acid

A. 2-Ethoxy-1-fluoro-3-(3-methoxyphenyl)prop-2-ene

2-Ethoxy-1-fluoro-3-(3-methoxyphenyl)prop-2-ene is prepared via 3-methoxyphenyl triphenylphosphonium bromide and ethylfluoroacetate using the method described in Steps A and B of Example 11.

B. 1-Fluoro-3-(3-methoxyphenyl)-2-propanone

2-Ethoxy-1-fluoro-3-(3-methoxyphenyl)prop-2-ene (8.40 g, 0.040 mol) is stirred with a saturated solution of hydrogen chloride in diethyl ether (80 ml) overnight. The ether layer is separated, washed with water, dried (MgSO$_4$) and filtered. Concentration of the solvent affords 1-fluoro-3-(3-methoxyphenyl)-2-propanone (7.200 g); NMR (CDCl$_3$): 3.73 ppm (m, 5H); 4.77 ppm (d, J$_{HF}$=48 Hz, 2H); 6.57–7.33 ppm (m, 4H).

C. 2-Amino-2-fluoromethyl-3-(3-methoxyphenyl)propionitrile

A mixture of 1-fluoro-3-(3-methoxyphenyl)-2-propanone (7.00 g, 0.038 mol), ammonium chloride (4.06 g, 0.076 mol) and 28% aqueous ammonia (50 ml) is treated with sodium cyanide (3.72 g, 0.076 mol), and the mixture is stirred at room temperature for 2 days, under nitrogen. The oil which separates is removed and extracted with diethyl ether, and the ethereal extract is washed with a saturated solution of sodium chloride in water, dried (MgSO$_4$), and filtered. Evaporation of the ether leaves an oily residue (6.90 g) which consists mainly of the required 2-amino-2-fluoromethyl-3-(3-methoxyphenyl)propionitrile as shown by NMR analysis.

D. 2-Amino-2-fluoromethyl-3-(3-hydroxyphenyl)propionic acid

A solution of the crude 2-amino-2-fluoromethyl-3-(3-methoxyphenyl)propionitrile (4.80 g, 0.023 mol) in 47% aqueous hydrobromic acid (50 ml) is heated under nitrogen, at 100° C. for 20 hours. The solution is evaporated to dryness under reduced pressure, the residue is taken up in isopropanol, and insoluble ammonium bromide is removed by filtration. Triethylamine is added to the filtrate until the pH reaches 5. The precipitated solid is collected, washed with chloroform, and recrystallized from water to give 2-amino-2-fluoromethyl-3-(3-hydroxyphenyl) propionic acid (2.59 g), m.p. 227° C.

EXAMPLE 10

Preparation of a Tablet Formulation

An illustrative composition for tablets is as follows:

|     |                                                     | Per Tablet |
|-----|-----------------------------------------------------|------------|
| (a) | 2-Amino-2-fluoromethyl-3-(3,4-dihydorxyphenyl)propionic acid | 250 mg     |
| (b) | Diacetoxydopamine                                   | 250 mg     |
| (c) | Wheat starch                                        | 15 mg      |
| (d) | Lactose                                             | 83.5 mg    |
| (e) | Magnesium stearate                                  | 1.5 mg     |

The granulation obtained upon mixing lactose, starch and granulated starch paste is dried, screened and mixed with the active ingredient and magnesium stearate. The mixture is compressed into tablets weighing 600 milligrams each.

EXAMPLE 11

Preparation of a Capsule Formulation

An illustrative composition for hard gelatin capsules is as follows:

|     |                                                     | Per Tablet |
|-----|-----------------------------------------------------|------------|
| (a) | 2-Amino-2-fluoromethyl-3-(3,4-dihydroxyphenyl)propionic acid | 300 mg     |
| (b) | Dopamine-glycyl peptide                             | 200 mg     |
| (c) | Talc                                                | 35 mg      |

The formulation is prepared by passing the dry powders of both (a) and (b) through a fine mesh screen and mixing them well. The powder is then filled into No. 0 hard gelatin capsules at a net fill of 535 mg per capsule.

In a similar fashion, a soft gelatin capsule is prepared in which the talc is omitted. The dry powders can be filled directly as a granulation, slug or compressed tablet into a rotary dye or plate mold in which the soft gelatin capsule is formed.

EXAMPLE 12

Preparation of Parenteral Formulation

An illustrative composition for a parenteral injection is the following emulsion:

| Each ml contains | Ingredients | Amount |
|------------------|-------------|--------|
| 50 mg            | 2-Amino-2-fluoromethyl-3-(3,4-dihydroxyphenyl)propionic acid | 1.000 g |
| 5 mg             | Dopamine                               | 0.100 g |
| 100 mg           | Polyoxyethylene sorbitan monooleate    | 2.000 g |
| 64 mg            | Sodium chloride                        | 0.128 g |
|                  | Water for injection, q.s.              | 20.000 ml |

The parenteral composition is prepared by dissolving 0.64 g of sodium chloride in 100 ml of water for injection, mixing the polyoxyethylene sorbitan monooleate with the 2-amino-2-fluoromethyl-3-(3,4-dihydroxyphenyl)propionic acid and dopamine, adding a sufficient solution of the sodium chloride in water to the active ingredient and polyoxyethylene sorbitan monooleate to bring the volume to 20 ml, shaking the mixture, and finally autoclaving the mixture for 20 minutes at 110° C., at 15 p.s.i.g. steam pressure. The composition can be dispensed either in a single ampule for subsequent use in multiple dosage or in groups of 10 and 20 ampules for a single dosage administration.

EXAMPLE 13

An illustrative composition for intramuscular injection is the following 1 ml ampul.

|     |                                                     | Weight percent |
|-----|-----------------------------------------------------|----------------|
| (a) | 2-Amino-2-fluoromethyl-3-(3,4-dihydroxyphenyl)propionic acid | 1.0 |
| (b) | Dopamine                                            | 0.1            |
| (c) | Polyvinylpyrrolidone                                | 0.5            |
| (d) | Lecithin                                            | 0.25           |
| (e) | Water for injection to make                         | 100.0          |

The materials (a) to (e) are mixed, homogenized, and filled into 1 ml ampuls which are sealed and autoclaved 20 minutes at 121° C. Each ampul contains 10 mg per ml of 2-amino-2-fluoromethyl-3-(3,4-dihydroxyphenyl)propionic acid and 1 mg per ml of dopamine.

EXAMPLE 14

The ability of a compound of Formula I to inhibit AADC enzyme can be demonstrated in vitro according to the following procedure:

AADC can be purified from hog kidney by the general method of J. Christenson et al. *Archs. Biochem. Biophys.*, 141, 356 (1970) and G. Lancaster et al., *Can. J. Biochem.*, 50, 791 (1972), and the specific activity of the enzyme is determined by the $^{14}CO_2$ trapping method using DL-[1-$^{14}$C]-dopa as the substrate (see Christenson et al.). One unit of activity is defined as the total amount of enzyme which produces 1 n mol of $CO_2$ per minute, with DL-[1-$^{14}$C]-dopa as substrate.

To 100 μl of 50 mM-phosphate buffer pH 7.4 containing 100 mM-mercapto-ethanol are added 5 μl of an aqueous solution containing the test compound at the desired concentration and 50 μl of an aqueous solution containing 2 units of AADC. The mixture is incubated at 37° C. and 20 μl aliquots are removed at various times. The AADC activity remaining in each aliquot is measured by the $CO_2$ trapping method of Christenson.

The results of the testing of representative compounds of Formula I are shown in Table I below, where the activity is shown by the time necessary to effect 90% inhibition of the enzyme. The relative activities of the compounds are rated by the given number of "plus" signs.

TABLE I $$X-CH_2-\underset{\underset{NH_2}{|}}{\overset{\overset{CH_2F}{|}}{C}}-COR_2$$

| COMPOUND X | $R_2$ | CONC. (μM) | TIME OF 90% INACTIVATION (min) | RATING |
|------------|-------|------------|-------------------------------|--------|
| 3,4-diOH-phenyl | OH | 10  | 1–2  | ++++ |
| 2,3-diOH-phenyl | OH | 10  | 1–2  | ++++ |
| 2,5-diOH-phenyl | OH | 10  | 3    | ++++ |
| 3-OH-phenyl     | OH | 100 | 4    | +++  |
| 4-OH-phenyl     | OH | 100 | >300 | 0–+  |
| 2-OH—4-methyl phenyl | OH | 100 | 1 | +++ |
| 2-OH—3-methyl phenyl | OH | 100 | 1 | +++ |

EXAMPLE 15

The effect of administering repeated doses of a compound of Formula I upon AADC activity and upon the catecholamine content in various body organs (e.g. brain, heart, and kidney) can be demonstrated by the following test procedure:

The test animals (e.g. mice or rats) are given the test compound in a suitable vehicle, either orally or by injection, each day over the period of time desired. The animals are kept on a constant time cycle, and body weights are measured daily. The animals are sacrificed by decapitation 12 to 24 hours after receiving the last dose of the test compound. Control animals receive the vehicle alone.

Immediately after death, the organs (brain, heart, and kidney) are removed and homogenized either in 50 ml phosphate buffer pH 6.8 for AADC determination or in ice-cold 0.4 M $HClO_4$ containing 0.05% (w/v) EDTA and 0.1% (w/v) sodium bisulfite for catecholamine determination. AADC activity is determined by the $^{14}CO_2$ trapping method of J. Christenson, supra (see Example 14) using DL-[1-$^{14}$C]-dopa as the substrate. Catecholamines are determined by centrifuging the homogenate, adding the supernatant to alumina buffered to pH 8.0–8.4 to adsorb the catecholamines, re-extracting the catecholamines from the alumina with 0.2 M $HClO_4$ and determining the catecholamines in the extracts using known procedures, such as by reversed-phase ion-pair HPLC with electrochemical detection.

Table II, shown below, sets forth the results obtained by testing particular compounds of Formula I in the above-described procedure in mice (Swiss Albino) after i.p. administration of the compound twice daily for three days:

TABLE II

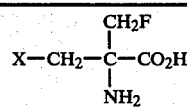

| COMPOUND X | DOSE (a) (mg/kg) | % CHANGE (b) AADC Brain | AADC Kidney | NOREPINEPHRINE Brain | NOREPINEPHRINE Heart | DOPAMINE Brain |
|---|---|---|---|---|---|---|
| 3-OH—phenyl | 10 | −80 | −78 | −34 | 0 | 0 |
|  | 100 | −95 | −96 | −77 | −49 | −75 |
| 2,3-diOH phenyl | 10 | −73 | −90 | −33 | −33 | −25* |
|  | 100 | −99 | −90 | −90 | −90 | −93 |
| 2,5-diOH phenyl | 10 | −58 | −78 | 0 | −25* | 0 |
|  | 100 | −99 | −87 | −90 | −76 | 90 |
| 3,4-diOH phenyl | 10 | −86 | −95 | −55 | −39 | 0 |
|  | 100 | −99 | −99 | −80 | −80 | −80 |
| 2-OH, 3-methyl phenyl | 10 | −52 | −84 | −27 | −41 | −20 |
|  | 100 (d) | −94 | −98 | −47 | −68 | −24 |
| 2-OH, 4-methyl phenyl | 10 | −39 | −70 | 0 | −7* | −9* |
|  | 100 (e) | −99 | −99.5 | −69 | −75 | −35* |
| 4-OH—phenyl | 100 (c) | −88 | — | −54 | −45 | −88 |

*Not significant
(a) Compound administered i.p. as water solution (1 ml/100 g)
(b) Change from control values; animals sacrificed 12 hours after receiving 6th dose
(c) Tested in rats
(d) 1/5-dead
(e) 2/5-dead Table III gives the results obtained by testing particular compounds of Formula I in rats (Sprague-Dawley) after oral administration of the test compound once daily for 15 days. AADC activity was not determined.

TABLE III

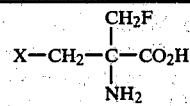

|  |  |  | % CHANGE |  |
|---|---|---|---|---|
|  |  |  | Brain |  |
| X | Dose (mg/kg) | Heart Norepinephrine | Norepinephrine | Dopamine |
| 3,4-diOH—phenyl | 5 | −56 | −25 | −2* |
|  | 10 | −67 | −47 | −8* |
|  | 15 | −68 | −51 | −6* |
|  | 20 | −72 | −49 | −10* |
| 2,3-diOH—phenyl | 10 | −38 | −11 | 0 |
|  | 20 | −48 | −17 | +3* |
|  | 30 | −79 | −27 | −10* |
| 2,5-diOH—phenyl | 10 | −31 | −16 | −1* |
|  | 20 | −38 | −32 | −2* |
|  | 30 | −53 | −37 | −5* |

*Not significant
(a) Compound administered in 1% ascorbic acid (5 ml/kg) by gavage
(b) Change from control values; animals sacrificed 24 hours after receiving 15th dose.

EXAMPLE 16

The effects of methyl 2-amino-2-fluoromethyl 3-(4-hydroxyphenyl)propionate on AADC inhibition and catecholamine levels in various organs can be demonstrated by the procedure of Example 15. When tested at doses varying from 5 to 200 mg/kg in fasted rats which were sacrificed 16 hours after receiving a single dose of the compound, the compound produced a marked decrease in AADC activity in kidney, liver, and adrenals at a dose of 50 mg/kg. Complete inhibition occurred at 100 mg/kg. In the brain, doses of 10 mg/kg and 200 mg/kg produced a 10% reduction and a 70–80% reduction of AADC activity, respectively. AADC activity in the heart is not reduced significantly, however, up to a dose of 200 mg/kg. Brain norepinephrine was decreased 15–20% and 50% at doses of 10 mg/kg and 200 mg/kg, respectively, while dopamine was decreased significantly at a dose of 50 mg/kg and 75% at 200 mg/kg. In the heart, no reduction of norepinephrine is noted up to a dose of 200 mg/kg. When tested after multiple administration of 10, 25, or 50 mg/kg given daily for six days in rats sacrificed 24 hours after the sixth dose, the compound produced a 50% decrease in brain norephinephrine at a dose of 10 mg/kg (daily). Higher doses do not give an additional response. Brain dopamine is decreased 50% at a dose of 50 mg/kg, but no significant effect is noted at lower doses. Serotonin (5-HT) levels, as assessed by standard techniques, are not altered in the brain even at the highest dose tested. Heart norepinephrine is reduced by only 20% at the highest dose.

EXAMPLE 17

The following example illustrates the effect of 2-amino-2-fluoromethyl-3-(3,4-dihydroxyphenyl)propionic acid on catecholamines and 5-HT in the brain.

Male Sprague-Dawley rats (200–300 g) from Charles River, France are housed in groups having free access to food and water. The animals are maintained on a 12 hour light-dark cycle at an ambient temperature of 23° C. The compound 2-amino-2-fluoromethyl-3-(3,4-dihydroxyphenyl)propionic acid is dissolved in 0.9% saline solution and administered as a single dose of 100 mg/kg, i.p. The animals are sacrificed 24 hours later and the brain is dissected on a chilled glass plate into six regions: the striatum, hypothalmus, olfactory tubercles, frontal cortex, cerebellum and brain stem. The tissues are weighed and homogenized in 600 microliters of ice-cold 0.4 Normal $HClO_4$ reagent. The homogenate is centrifuged and dopamine, noradrenalin and 5-hydroxytryptamine are determined by reversed-phase ion-pair high pressure liquid chromatography using electrochemical detection. The following results are obtained as shown in Table IV.

TABLE IV

Effect of 100 mg/kg, i.p. of 2-amino-2-fluoromethyl-3-(3,4-dihydroxyphenyl)propionic acid on catecholamine content of various brain regions of the rat after 24 hours post-dose (ng/g ± S.E.M.)

| Brain Area | Treatment | Dopamine | Noradrenaline | 5-Hydroxytryptamine |
|---|---|---|---|---|
| Striatum | control | 7342 ± 357 | 47 ± 13 | 591 ± 47 |
| | compound | 1466 ± 156*** | 46 ± 24 | 50 ± 16*** |
| Hypothalamus | control | 399 ± 23 | 1419 ± 107 | 1162 ± 306 |
| | compound | 280 ± 69 | 631 ± 37** | 199 ± 44* |
| Olfactory Tubercles | control | 1954 ± 62 | 360 ± 32 | 699 ± 72 |
| | compound | 403 ± 44*** | 126 ± 29** | 87 ± 31** |
| Frontal Cortex | control | — | 160 ± 23 | 365 ± 23 |
| | compound | — | — | 19 ± 7*** |
| Cerebellum | control | — | 137 ± 1 | 30 ± 3 |
| | compound | — | 17 ± 3*** | 11 ± 3** |
| Brain Stem | control | 37 ± 9 | 439 ± 47 | 620 ± 35 |
| | compound | 13 ± 4 | 143 ± 9** | 136 ± 50** |

*$p < 0.05$
**$p < 0.01$
***$p < 0.001$

EXAMPLE 18

The following example illustrates the effect of repeated administration of 2-amino-2-fluoromethyl-3(3,4-dihydroxyphenyl)propionic acid in the brain.

Male albino mice (25–30 g) from Charles River, France and dosed i.p. with 100 mg/kg of 2-amino-2-fluoromethyl-3-(3,4-dihydroxyphenyl)propionic acid every 12 hours for 5 doses. Saline solution is used as a control. The mice are sacrificed and the catecholamines, dopamine and noradrenaline, and serotonin (5-hydroxytryptamine) are determined by reverse-phase ion-pair high pressure liquid chromatography using electrochemical detection. The following results are obtained as shown in Table V.

TABLE V

Effect of repeated administration (5 × 100 mg/kg, i.p.) every 12 hours on the catecholamine content of the brain in mice (ng/g ± S.E.M.)

| Treatment | Dopamine | Noradrenaline | Serotonin |
|---|---|---|---|
| Saline | 722 ± 47 | 310 ± 15 | 1685 ± 29 |
| Test compound | 18.6 ± 2 | 19.6 ± 3 | 282 ± 25 |
| % Reduction | −97% | −94% | −83% |

The above data shows that the dopamine content of the mouse brain is reduced by 97%, the noradrenaline content is reduced by 94%, and the serotonin content of the brain is reduced by 83%.

EXAMPLE 19

The following example illustrates the effect of dopamine administration on the depletion of catecholamines in heart and brain of mice treated with two doses of 100 mg of 2-amino-2-fluoromethyl-3-(3,4-dihydroxyphenyl)propionic acid.

Male albino mice (25-30 g) from Charles River, France had been injected i.p. with 2 doses of 100 mg of 2-amino-2-fluoromethyl-3(3,4-dihydroxyphenyl)propionic acid at 12 hours interval. Twelve hours after the second dose, one group of animals received an i.p. injection of 50 mg/kg of dopamine-HCl (Sigma, Chem. Co), the other group received saline instead. Three hours after the dopamine injection, the animals were killed and catecholamines were measured in heart and brain as described in Example 18. The results are shown in Table VI.

TABLE VI

Effect of dopamine injection (50 mg/kg, i.p.) on catecholamine levels in heart and brain of mice treated with two doses of 100 mg/kg of a test compound (ng/g ± SEM; n = 5)

| | Brain | | Heart | |
|---|---|---|---|---|
| Treatment | Dopamine | Noradrenaline | Dopamine | Noradrenaline |
| Control | 1183 ± 28 | 516 ± 24 | 20 ± 2 | 760 ± 87 |
| 2 × 100 mg/kg test compound + saline | 47 ± 5* | 44 ± 6* | 98 ± 62 | 173 ± 24* |
| 2 × 100 mg/kg test compound | 92 ± 8* | 42 ± 4* | 429 ± 39* | 882 ± 47 |

TABLE VI-continued

Effect of dopamine injection (50 mg/kg, i.p.) on catecholamine levels in heart and brain of mice treated with two doses of 100 mg/kg of a test compound (ng/g ± SEM; n = 5)

| Treatment | Brain | | Heart | |
|---|---|---|---|---|
| | Dopamine | Noradrenaline | Dopamine | Noradrenaline |
| + dopamine | | | | |

*$P > 0.01$ (compound with control)

These data show that the depletion of noradrenaline in the heart achieved by the test-compound can be reversed totally by the dopamine injection. The depletion of amines in the central nervous system is not affected by the exogenous dopamine.

What is claimed is:

1. A method for selectively depleting endogenous central nervous system monoamines useful for controlling certain neuropsychiatric disorders in mammals in need thereof, said disorders consisting of schizophrenia, mania, tardive dyskinesia, anxiety, or depression, which comprises administering to said mammals:
   (a) from 0.25 mg/kg to 100 mg/kg of a compound of the formula:

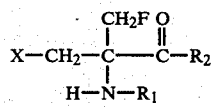

wherein:
$R_1$ is hydrogen, ($C_1$-$C_4$alkyl)carbonyl, or

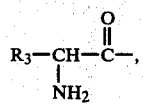

wherein $R_3$ is hydrogen, $C_1$-$C_8$alkyl, benzyl, or 4-hydroxybenzyl;
$R_2$ is hydroxy, $C_1$-$C_8$ alkoxy, amino, ($C_1$-$C_4$alkyl)amino, di($C_1$-$C_4$alkyl)amino, or

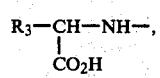

wherein $R_3$ is hydrogen, $C_1$-$C_8$alkyl, benzyl, or 4-hydroxybenzyl;
X is a substituted phenyl group of the formula:

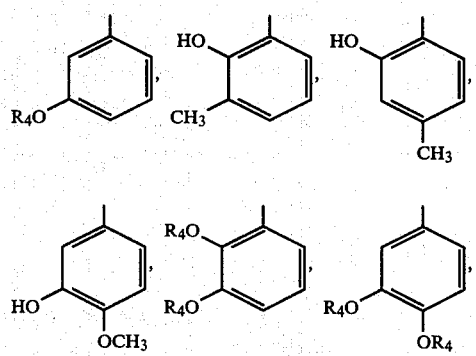

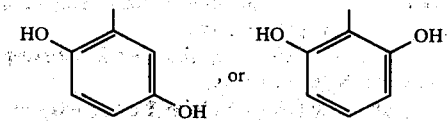

wherein $R_4$, as defined by X, is hydrogen, ($C_1$-$C_4$alkyl)carbonyl, benzoyl, or phenyl($C_1$-$C_6$alkylene)carbonyl; and the pharmaceutically acceptable salts thereof; and the individual optical isomers thereof; with
   (b) from 0.01 mg/kg to 100 mg/kg to dopamine.

2. A method as defined in claim 1 wherein X is:

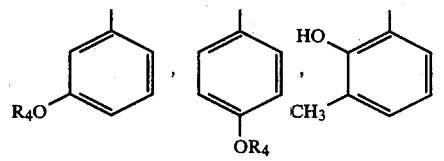

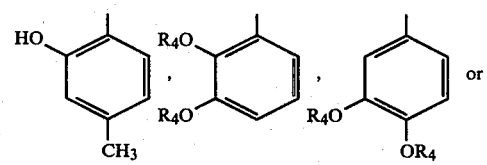

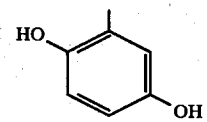

3. A method as defined in claim 2, wherein the compound administered is 2-amino-2-fluoromethyl-3-(3,4-dihydroxyphenyl)propionic acid.

4. A method as defined in claim 2, wherein the compound administered is 2-amino-2-fluoromethyl-3-(2,3-dihydroxyphenyl)propionic acid.

5. A method as defined in claim 2, wherein the compound administered is 2-amino-2-fluoromethyl-3-(2,5-dihydroxyphenyl)propionic acid.

6. A method as defined in claim 2, wherein the compound administered is 2-amino-2-fluoromethyl-3-(3-hydroxyphenyl)propionic acid.

7. A method as defined in claim 2, wherein the compound administered is 2-amino-2-fluoromethyl-3-(2-hydroxy-3-methylphenyl)propionic acid.

8. A method as defined in claim 2, wherein the compound administered is 2-amino-2-fluoromethyl-3-(2-hydroxy-4-methylphenyl)propionic acid.

9. A method as defined in claim 2, wherein the compound administered is 2-amino-2-fluoro-3-(4-hydroxyphenyl)propionic acid.

10. A method as defined in claim 2, wherein the compound administered is methyl 2-amino-2-fluoromethyl-3-(4-hydroxyphenyl)propionate.

11. A method as defined in claim 2, wherein the compound administered is ethyl 2-amino-2-fluoromethyl-3-(4-hydroxyphenyl)propionate.

12. A method as defined in claim 1, wherein the compound administered is 2-amino-2-fluoromethyl-3-(3-hydroxy-4-methoxyphenyl)propionic acid.

13. A method as defined in claim 1, wherein the compound administered is 2-amino-2-fluoromethyl-3-(2,6-dihydroxyphenyl)propionic acid.

14. A method as defined in claim 1 or 2, wherein $R_1$ is hydrogen and $R_2$ is hydroxy.

15. A method as defined in claim 1 or 2, wherein $R_1$ and $R_4$ are hydrogen.

16. A method as defined in claim 1 or 2, wherein $R_1$ is hydrogen, $R_2$ is $C_1$–$C_8$alkoxy, and $R_4$ is hydrogen.

17. A method as defined in claim 1 or 2, wherein $R_2$ is hydroxy and $R_4$ is hydrogen.

18. A method as defined in claim 1, 2, 3, 4, 5, 6, 7, 8, 9, 10, 11, 12, or 13 wherein the mammal is a human.

19. A method as defined in claim 1, 2, 3, 4, 5, 6, 7, 8, 9, 10, 11, 12, or 13 wherein the neuropsychiatric disorders are schizophrenia, mania, tardive dyskinesia, or anxiety.

* * * * *